(12) United States Patent
Sauter

(10) Patent No.: US 7,757,573 B2
(45) Date of Patent: Jul. 20, 2010

(54) BED WATER SAMPLING DEVICE

(75) Inventor: Eberhard J. Sauter, Ritterhude (DE)

(73) Assignee: Stiftung Alfred-Wegener-Institut Fuer Polar-und Meeresforschung, Bremerhaven (DE)

( * ) Notice: Subject to any disclaimer, the term of this patent is extended or adjusted under 35 U.S.C. 154(b) by 787 days.

(21) Appl. No.: 10/520,826

(22) PCT Filed: Jul. 13, 2003

(86) PCT No.: PCT/DE03/02399

§ 371 (c)(1),
(2), (4) Date: Jul. 11, 2005

(87) PCT Pub. No.: WO2004/010111

PCT Pub. Date: Jan. 29, 2004

(65) Prior Publication Data

US 2007/0113687 A1 May 24, 2007

(30) Foreign Application Priority Data

Jul. 14, 2002 (DE) ................................ 102 32 623

(51) Int. Cl.
*G01N 1/12* (2006.01)
*G01N 1/16* (2006.01)

(52) U.S. Cl. .............. 73/864.65; 73/863.31; 73/863.71; 73/864.66

(58) Field of Classification Search . 73/864.65–864.66, 73/864.63, 863.31, 863.71
See application file for complete search history.

(56) References Cited

U.S. PATENT DOCUMENTS

| | | | |
|---|---|---|---|
| 3,368,408 A * | 2/1968 | Mangin | 73/864.67 |
| 3,950,999 A | 4/1976 | Edwards | |
| 4,089,209 A * | 5/1978 | Grana et al. | 73/61.41 |
| 5,343,768 A | 9/1994 | McClane | |
| 5,364,297 A * | 11/1994 | Rohardt | 441/23 |
| 5,460,056 A | 10/1995 | Phillips | |
| 5,473,952 A * | 12/1995 | Lieberman et al. | 73/864.31 |
| 2003/0070499 A1* | 4/2003 | Pratt | 73/864.63 |
| 2004/0173035 A1* | 9/2004 | Britt | 73/864.66 |
| 2004/0237672 A1* | 12/2004 | Jaeger | 73/863.31 |

FOREIGN PATENT DOCUMENTS

DE            1598268 A1       12/1970

(Continued)

OTHER PUBLICATIONS

"PROVESS" Process of Vertical Exchange in Shelf Seas—MAST III (see. PROVESS homepage by Rose Player, Proudman Oceanographic Laboratory, at http://www.pol.ac.uk/provessl/html/main.html, last updated on Apr. 17, 2001, photographic link theron last updated Apr. 15, 1999 to photograph of Bottom water sampler dated Nov. 1998.*

L. Thomsen et al. "An instrument for aggregate studies in the benthic boundary layer", Marine Geology 135, 1996, Elsevier Science, pp. 153-157.

(Continued)

*Primary Examiner*—Thomas P. Noland
(74) *Attorney, Agent, or Firm*—Leydig, Voit & Mayer, Ltd.

(57) ABSTRACT

A bed water sampling device in which a plurality of horizontally oriented tubular sampling containers are mounted on a member adjustable in its position in response to the direction of water current and in which the tubular sampling containers are provided with valves simultaneously moved from their open to their closed states in response to a signal generated in response to placement of the sampling device on the water bed.

17 Claims, 2 Drawing Sheets

FOREIGN PATENT DOCUMENTS

| | | | |
|---|---|---|---|
| DE | 2856245 | A1 | 11/1980 |
| DE | 19515952 | A1 | 11/1995 |
| DE | 29621644 | U * | 2/1997 |
| DE | 19750268 | A1 | 6/1998 |
| FR | 2286377 | A1 | 4/1976 |
| JP | 54026785 | A * | 2/1979 ............. 73/863.31 |
| JP | 2000144701 | A * | 5/2000 |
| JP | 2002161693 | A * | 6/2002 |
| SU | 637620 | A * | 12/1978 |
| SU | 732723 | A * | 5/1980 |
| SU | 1137881 | A * | 3/1993 |

OTHER PUBLICATIONS

Laurenz Thomsen, "Processes in the benthic boundary layer at continental margins and their implication for the benthic carbon cycle", Journal of Sea Research 41, Elsevier Science, 1999, pp. 73-86.

Alena Mudroch et al. "Handbook of Techniques for Aquatic Sediments Sampling", second edition, pp. 105-106 by Jun. 2009.

* cited by examiner

BED WATER SAMPLING DEVICE

BACKGROUND OF THE INVENTION

1. Field of the Invention

The invention relates to a bed water sampling device for simultaneously taking several water samples from the lowest column of water at different heights above the water bed by several cylindrical sample containers which at least one of their front surfaces are provided with a closure actuated by a time-controlled release and which are horizontally oriented for vertical adjustment on a central support rod which terminates in a bottom element and which may be deposited on the water bed by a steel cable attached to its opposite end.

The taking of water samples from the lowest water column, i.e. the bed water above the water bed serves geochemical, oceanographic and (micro-) biological investigations of the transition zone between the water bed (sediment) and the column of water disposed above it. Different exchange processes between these separate sections generate steep gradients of parameters, e.g. in geochemical material concentrations and particle contents which often are very closely intermingled with biological life processes. A bed water sampling device should make high-resolution sampling possible, i.e. sampling at several levels above the bottom of the body of water, the transition zone, in order to allow new insights into the transport and reaction processes prevailing there.

2. The Prior Art

Basically, a distinction has to be made between two types of bed water sampling devices: Arrangements which draw in the water samples from different levels above ground and those in which the water is "caught" by sampling containers arranged at different levels above ground, usually in a horizontal orientation. Among the first mentioned group (taking samples by suction) is, for instance, the water scoop (BIO-PROBE) for depths of water up to 600 m in which several sample bottles are vertically arranged on a tripod frame, as mentioned in publication I by L. Thomsen et al.: "An instrument for aggregate studies in the benthic boundary layer" (Marine Geology, 135 (1996), pp. 153-156). Water samples are drawn into the bottles from different levels of the water column by means of suction hoses of different lengths. The disadvantage of this is that while bed water particles may be sampled, their original condition is disturbed by suction of the water samples through the suction hose. Also, the water sample may be subjected to degasification during the suction operation. However, gases dissolved in water often are parameters to be examined. The sample scoop is activated from the water surface, usually from a ship, by a single conductor cable. Since the sampling lasts a relatively long time (30 to 60 minutes), drifting of the ship during the sampling operation may lead to damage of the single conductor cable as a result of twisting. Repairing the single conductor cable by shortening it and renewed placement of the deep sea probe is both very time consuming and expensive. The cable cannot be used for a day otherwise available for taking measurements. Even if the sampler is mounted on a wide-spread tripod frame to minimize current-conditioned eddying and, hence, mixing of the water samples originating from different horizons, its action cannot be avoided altogether. In addition, the suction snorkels themselves constitute flow impediments, so that higher sampling horizons in particular are affected by flow dynamics of any of the more deeply suspended snorkels.

Modifications of the known BIOPROBE water scoop may be gleaned from publication II by L. Thomsen: "Processes in the benthic boundary layer at continental margins and their implication for the benthic carbon cycle" (Journal of Sea Research 41 (1999), pp. 73-86). In BIOPROBE III a hydrodynamically shaped sampler is eccentrically mounted on a mechanically rotatable arm which for the avoidance of mixed sampling is aligned before sample taking in the benthic current by a current sensor. The sampler is vertically arranged and is provided with four sample chambers of 10 l capacity and intake nozzles through which the sample water flows in, at different but rigidly defined levels within a relatively small range of heights (between 5 and 40 cm). However, the principle of nozzles still renders the taking of samples free of particles and without loss of gasses as well as prior rinsing of the sample containers by original bed water problematic. Although current from a battery renders BIOPROBE III self-contained so that it may be used without a single-conductor cable, yet since it is dropped into the water as a free falling apparatus (lander), its recovery operations are time-consuming.

The most closely related state of the art, upon which the present invention is based, is a bed water sampler with an arrangement of horizontally oriented sample containers as described by A. Murdoch et al. in their book "Handbook of Techniques for Aquatic Sediments Sampling", $2^{nd}$ edition, pp. 105-106. In this deep sea bed water sampler, several sample bottles structured as cylindrical sample containers, each of 3 l capacity, are mounted and secured against rotation on a central aluminum rod and arranged at different heights changeable over a range of 1.6 m. For its stabilization the central support rod is rigidly mounted on a bottom plate functioning as a bottom element and is supported by three cantilevers. The cantilevers are in turn tensioned by wire cables to a tripod at the upper end of the support rod. This is were a simple wire cable for lowering the sampler is also attached. While it is being lowered, the sampler and, with it, all the sample bottles are not aligned with the current. At one of their end surfaces, the sample bottles are provided with a closure structured as a slidable piston bottom. Their sliding motion is induced pneumatically by a bottle of compressed gas and is controlled by a pressure-protected electronic time release. The sample bottles are to be filled with sample water by way of the piston bottom which results in backup pressure in the interior of the bottle, however, and which may cause disturbance in the taking of the samples such as, for instance, loss of dissolved gasses. Further disturbance during the taking of samples may be caused by the sample bottles not being aligned in the direction of the current so that the sample containers cannot be flushed out by original bed water and by the support cables of the support rod disturbing the current which may lead to mixed samples as a result of eddying.

A bed water sampler with horizontally oriented through-flow sample bottles is known from the joint program of several countries "PROVESS"—Process of Vertical Exchange in Shelf Seas—MAST III (see. PROVESS homepage by Rose Player, Proudman Oceanographic Laboratory, at http://www.pol.ac.uk/provess/html/main.html, last updated on 17 Apr. 2001, State as of 19 Jun. 2002 (see photograph on page http://pol.ac.uk/provess/phographs/b_w_sampler.gif, state 19 Jun. 2002. The photograph reveals ten horizontally oriented transparent sample bottles arranged in superposition on a support scaffold consisting of two parallel support rods centrally fixed in a flaring four-legged frame weighted down by bottom weights. Apparently, the sample bottles are at each end face provided with a closure lid which may be mechanically actuated by a cable mechanism. Hence, for taking samples, the water sample bottles may be freely flushed with water. Further details cannot be discerned from the photograph. Nor does the PROVESS homepage impart further details about the displayed sampler. It can be seen, however, that the sample bottles are rigidly connected to their support frame and that they are surrounded by the four-legged frame. It is, therefore, not possible precisely to align the sample bottles relative to the current for flushing with original bed water and to rinse away sedimentary particles which could have entered the containers while placing the device on the bed. Moreover, the bottom current is dynamically disturbed by the four-legged frame and its cross-braces, so that, again, mixed samples will develop as a result of eddying.

OBJECT OF THE INVENTION

Proceeding from the closest state of the art discussed supra, the object of the present invention is to be seen in improving a bed water sampling device of the kind under consideration for the simultaneous collection of several undisturbed samples of water from different levels of the lowest water column above the water bed by several horizontally oriented cylindrical sample containers so that undisturbed and high-resolution samples may be taken from the current adjacent to the bed in the material and particle containing transition zone between the water bed and the column of water while substantially maintaining the original state of the water to be sampled. The improved bed water sampling device is to make possible taking of samples as quickly as possible, and in terms of handling it is to be simple and robust. Moreover, particles stirred up when placing the sampling device on the water bed as well as water from other layers in the water column are to be flushed out of the containers by the original bed water prior to their closure.

SUMMARY OF THE INVENTION

In a bed water sampling device of the kind under consideration and described above, the object is accomplished in accordance with the invention by the center support rod being connected between the weighted base frame functioning as a bottom element and the steel cable at low friction and for free rotation and provided with a flow vane, by the time-controlled release being encapsulated in the weighted base frame in a compression-proof manner for automatic actuation only a predetermined period of time after the base frame has come to rest on the water bed and by the other end surface of the sample containers being also provided with a closure device actuated by the time-controlled release.

The bed water sampling device in accordance with the invention combines high functionality to accommodate high-value water sampling demands. To be mentioned among these is the taking of samples from different water horizons free of any admixture and without suction and with a particular degree of field suitability, especially in view of the fact that the submersion cable may be freely selected, that the dwell time on the bed is short and the resultant minimum requirements in terms of the position of the ship. In this respect, the relationship between the concept of the release for the simultaneous closure of all of the sample containers at both ends and their simple and automatic alignment with the bed is essential. Since both ends of the sample containers are open before the samples are collected, genuine bed water may freely flow through them. Thus, at the instance both ends of the sample containers are closed, a sample of water is trapped in its free state of flow and, therefore, substantially original state. Since the water samples are collected without suction, any error-generating loss of gas in the water sample otherwise caused by the lowered solubility of gases in water as a result of suction-generated negative pressure is avoided. Alignment in the current is brought about by a sufficiently large flow vane rigidly connected to the freely rotatable support rod. The size of the vane is dimensioned such that even weak currents in the bed water zone close to the bottom will suffice to rotate and align the sample container on the central support rod in the current.

Furthermore, the time-controlled release ensures the taking of samples in undisturbed current conditions. The sample containers are closed only after any disturbances caused by placing the measuring arrangement on the water bed have subsided. Automatic actuation of the release takes place mechanically by upward pressure acting on a release plate disposed beneath the heavy base frame for a sufficiently long period, for instance one minute. In this manner, premature closure of the sample containers resulting, for instance, when accidentally placing the sampling device aboard ship during a placement operation, is substantially avoided. Moreover, because of the entirely mechanical actuation there is no need for a sensitive line for feeding control pulses from the surface of the water. The closure devices of the sample containers are actuated by an integrated time control—this may, for instance, be an electronic timer which, depending on its pressure capsule, can be applied at depths of 6,000 m and beyond, for instance—upon its actuation after a select time delay, e.g. a few minutes after placement of the sampling device. Hence, two integrated time loops are provided for a secure and flawless operation of the bed water sampling device in accordance with the invention.

In order to disturb the bed as little as possible the structure of the bed water sampling device advantageously has no exterior braces or tension wire devices. Flow dynamic mixing of layers of bed water by artificial turbulence is avoided. The stable vertical position of the apparatus on the water bed is achieved, for instance, by a base frame weighted by lead ballast units. The bed water sampling device in accordance with the invention is suitable for deep sea operation and may, depending upon the stability of the pressure capsule of the release, be used in depths of water of 6,000 m and more. Overall, a bed dwell time of 5 minutes up to a maximum of 10 minutes is needed for taking samples. During a time interval of so short a duration it is possible without any difficulty sufficiently precisely to maintain the position of the ship relative to the sampling device so that entanglements of, or kinks in, the sinking steel cable occurring in consequence of veering made necessary by the ship moving because of wind or surface currents, may with a great degree of certainty be avoided.

An essential advantage of the bed water sampling device in accordance with the invention is the taking of bed water samples as undisturbed instantaneous records. For this purpose, it is important that initially the bed current may flow through the cylindrical sample container. The sample cylinders are, therefore, provided at both end surfaces with closure devices which in their open state expose a relatively large cross-section of the sample containers. In one embodiment of the bed water sampling device it is, therefore, advantageous to provide the two closure devices of each sample container with closure valves which in their open state are held in their open state against the bias of a return rubber tension device connected to a release shaft secured by a corrosive or burn wire. Subjecting the corrosive wire to an electrical voltage upon actuation of the time-controlled release causes it to rupture. Such a release arrangement is robust and reliable in its operation and may easily be set up on board the ship from which the sampling device is deposited. Initially, the closure valves are biased toward each by a rubber tension band which may, for instance, extend through the interior of the sample container and is fixed to a release shaft. The release shaft, in turn, is retained in its position by a burn wire. The burn wire is then charged with an electric current by the time-delayed actuation of the time-controlled release and after a further time delay following the placement of the sampling device on the bottom of the sea. In the well-conductive sea water the wire will corrode through in one to three minutes and release the release shaft thereby to cause all the closure valves to close simultaneously.

For purposes of a non-invasive taking of samples it is important that transfer of the water samples for subsequent examination onboard the ship take place with little mixing with air in order to prevent an unintentional absorption or discharge of gases from or into the atmosphere. In accordance with a further advantageous embodiment of the invention, every sample container may for this purpose be provided with a water discharge valve and, diametrically opposite, an air intake valve. In this manner, the air replacing the water flowing out of the container may uniformly flow into the container without any mixing of water and air. Any exchange of gas with the atmosphere is thus limited to a minimum. In accordance with a further embodiment of the invention the sample container are transparent. In this manner it is possible to obtain an indication of the particle content and particle structure in individual water samples during the taking of the samples have been taken, by a camera, for instance, or by photographing or visual inspection before the sample is discharged on board ship.

The bed water sampling device is suitable for great depths of water. Because of the pressure conditions prevailing at such depths, the water has a certain gas absorption capacity. In order to prevent degasification during transfer of the samples to areas of lower pressure (up to atmospheric pressure) the sample containers and both closure devices, in accordance with a further embodiment of the invention and as alternatives to the transparent kind, may be structured to be compression-proof. The complete preservation of the original condition of the water derived therefrom may lead to invaluable additional findings. Compression-proof sample containers for sea depths up to 6,000 m may be made of a compression-proof material, such as steel or special titanium alloys, in particular.

Samples from the bed water column should be taken at high resolution at about 2 m above ground at several water horizons with at least 5 l being required per horizon for an isotropic analysis. For that reason it is advantageous, in accordance with a further embodiment of the bed water sampling device, to array a total of six sampling containers at a height of 2 m with each container having a capacity of 5 to 6 l. Six sample containers lead to the sampling of six water horizons which extend at a vertical distance of about 30 cm relative to each other so as to ensure a high resolution of measurement of the vertical water column. At this point it is to be mentioned that the individual sample containers on the central support rod may be disposed at a constant as well as a variable spacing from each other. The number and positioning of the sample containers are dependent upon the resolution profile to be provided which in turn is a function of the occurring measuring parameters. Using 6 vertically adjustable and horizontally oriented sample containers of about 6 l capacity each, the individual water samples will each be taken from layers of water of a thickness of about 10 cm which while positioned sufficiently close to each other do not, however, influence each other.

Since the bed water sampling device in accordance with the invention does not use braces and tension wires which would interfere with the bed current, the stable vertical position of the apparatus is ensured by the base frame being weighted by ballast units made of lead, for instance. Furthermore, in another embodiment of the invention several buoyancy units may be attached to a steel cable above the sampling device. For instance, two buoyancy units may be mounted about 15 m above the sampling device, and in concert with the ballast units effectively prevent the bed water sampling device in accordance with the invention from overturning.

DESCRIPTION OF THE SEVERAL DRAWINGS

The novel features which are considered to be characteristic of the intention are set forth with particularity in the appended claims. The invention itself, however, in respect of its structure, construction and lay-out as well as its manufacturing techniques, together with other advantages and objects thereof, will be best understood from the following description of preferred embodiments when read in connection with the appended drawings, in which:

DETAILED DESCRIPTION OF THE PREFERRED EMBODIMENTS

Figure 1:
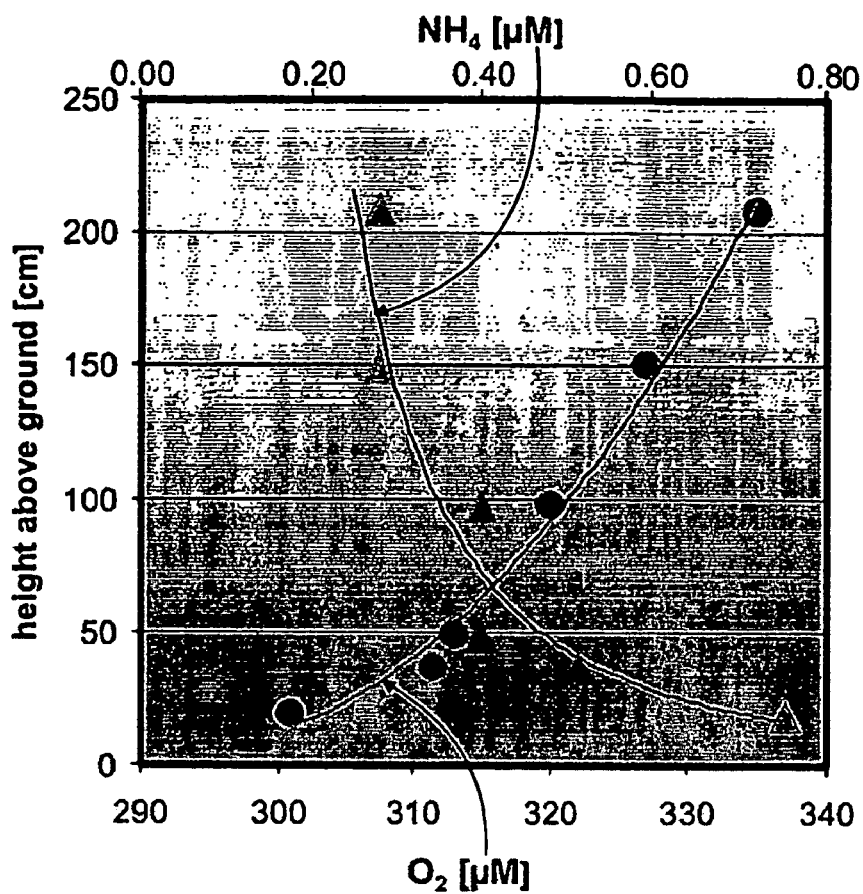
FIG. 1 are diagrams showing typical parametric curves.
Figure 1:
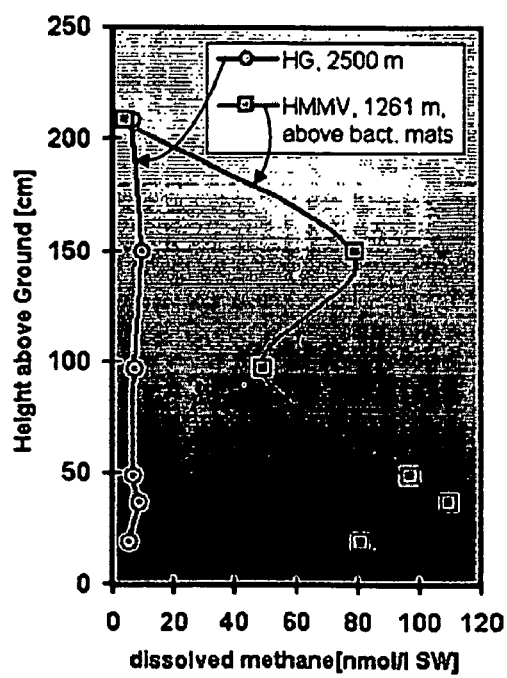

The main purpose of the bed water sampling device in accordance with the invention is to take vertically staggered samples of high-resolution quality so that profiles of vertical measurements may be provided. Especially in the transition zone between the bottom of the body of water and the water column disposed above it up to a range of about 2 m the measurement values to be recorded often display steep gradients. These may be seen, for instance, in FIG. 1 the upper diagram of which depicts the curve of the oxygen content $O_2$ and of the ammonium content $NH_4^+$ in μM (micro mol) above the height in cm above ground at a depth of 2,500 m at the measuring site "AWI-Hausgarten" west of Spitzbergen. By comparison, the lower diagram of FIG. 1 shows the content of dissolved methane (dissolved methane in nmol per l of sea water) in bed water, again at the "AWI-Hausgarten" site at a depth of 2,500 m (left curve, low values) and, additionally, above the "Hakon Mosby" mud volcano at a depth of 1,260 m (right curve, high values). The different parameter curves at different levels above a common deep sea sediment ("AWI-Hausgarten") and above the surface of the mud volcano, respectively, in the water column close to the bed may be clearly seen here which approximate each other only beginning at a level of about 2 m.

Figure 2:
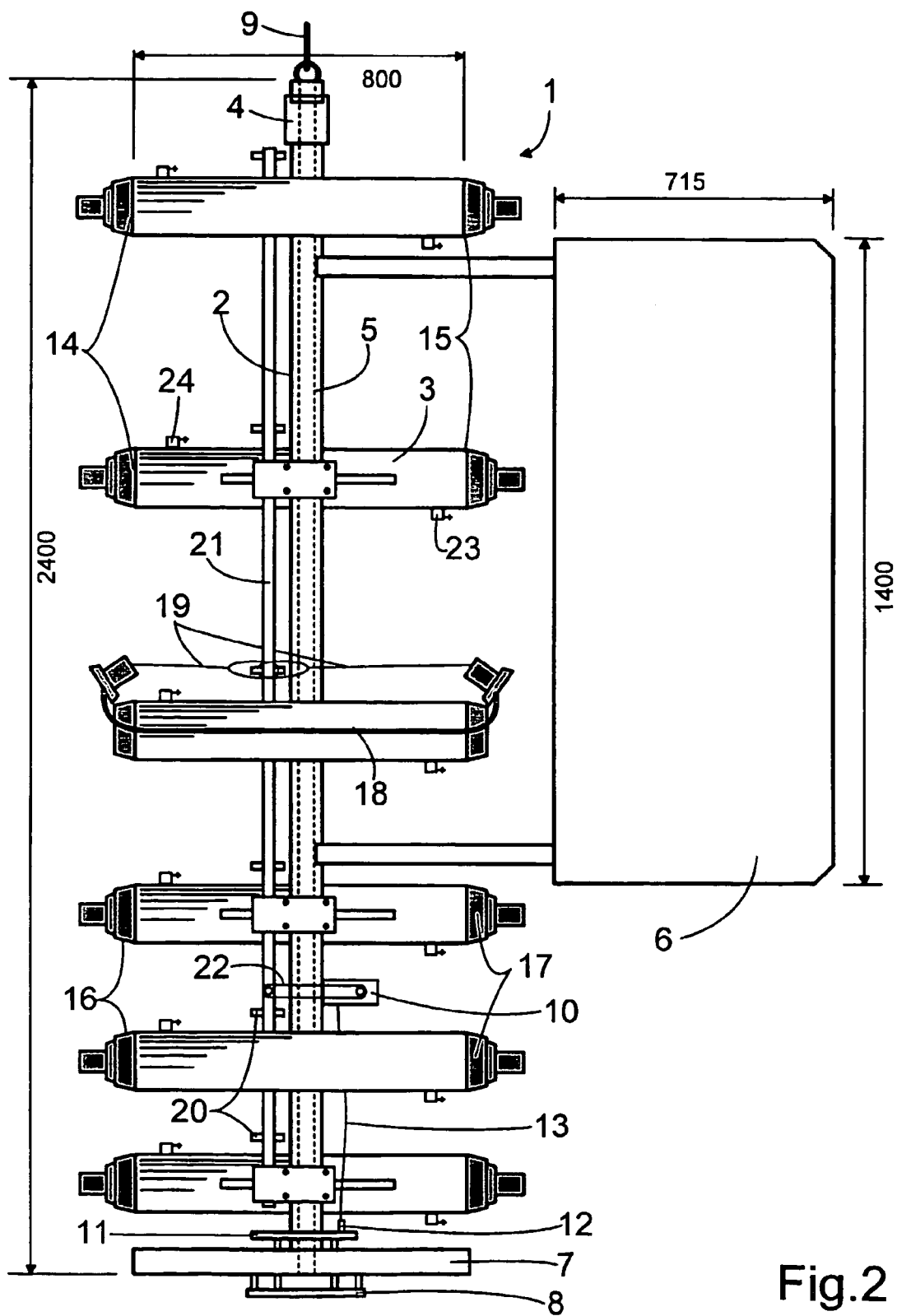
FIG. 2 depicts an embodiment of the bed water sampling device in accordance with the invention.

FIG. 2 shows a bed water sampling device 1 in accordance with the invention for simultaneously collecting several water samples at different levels from the lowest water column above a water bed (dimensions in mm). Six sample containers 3 are arrayed at different heights on a center support rod 2. In the selected embodiment, the distances increase upwardly over a length of 2 m so that a particularly high resolution may be realized in the lowest, close-to-the-bed layer of water. By means of a bearing 4, the center support rod 2 is journaled on a shaft 5 extending through it by means of a bearing 4, and is provided, for alignment with the water current near the bed, with a rectangular vane 6 which in the selected embodiment measures about 1 $m^2$. The lower end of the center shaft 5 is rigidly connected to a base frame 7 weighted by lead ballast. A vertically movable release plate 8 is provided in the center of the base frame 7. A common steel cable 9 is connected to the upper end of the center shaft 5 by means of a shackle. Several meters above the bed water sampling device 1, a buoyancy device, not shown in FIG. 2, is attached to the steel cable 9 for maintaining it vertically taut. The tautness and the weighted base frame 7 result in a secure vertical stationary position of the bed water sampling device 1. It is further augmented by an alternating arrangement of the sample containers 3 in front of and behind the center support rod 2.

The release plate 8 is connected to a time-controlled release 10 which following a predetermined time delay, for instance 1 minute, is activated by a slight but lasting upward pressure of the release plate 8 when positioning the bed water sampling device 1. In order not to interfere with the free rotatability of the center support rod 2 about the center shaft 5 by cable suspensions, the positioning signal furnished by the release plate 8 is transmitted by a slip ring 11 to a compression-proof magnetic contact 12 which transmits the signal by way of a submarine cable 13 to the time-controlled release 10. During lowering of the bed water sampling device 1 all sample containers 3, which in the selected embodiment are transparent cylinders, are open at both ends 14, 15 (shown in FIG. 2, by way of example, at one sample container 3). The sample containers 3 are each provided with two closure devices 16 with closure valves 17. In their open state, they are biased toward their closed position by a rubber tension device 18 extending through the interior of the sample container 3 but maintained in their open state by cords 19 connected to transverse bolts 20 on the release shaft 21 rotatable in the horizontal plane. The position of the release shaft 21 is secured by a corrosion wire 22. When the time-controlled release 10 is activated the corrosion wire 22 is subjected, after a dwell time electronically or mechanically set in the time control, to a voltage by way of an electrical line not shown in FIG. 2, and in the well-conducting sea water it will disintegrate within one to three minutes, depending upon the gage of the wire and the material of the wire. The release shaft 21 which is then no longer arrested in its position will rotate sufficiently under the tension of the rubber tension devices 18 of all the sample containers 3 for the transverse bolts 20 to release the cords 19 of the closure valves 17. As a result, the closure valves 17 will close both 14, 15 ends of the sample containers 3 almost simultaneously so that the bed water from the different water horizons instantaneously flowing through the sample containers 3 is trapped. The time-controlled release 10 is mechanically activated by the release plate 8; the corrosion voltage for releasing the closure device 16 is provided by a source of current integrated in the time-controlled release 10. The bed water sampling device 1 in accordance with the invention is thus self-contained and may be hoisted by the simple steel cable. No single conductor cable is required. For discharging the trapped bed water sample aboard ship without interference, the sample containers are provided with a water discharge valve 23 and, diametrically opposite, an air inlet valve 24. A sample storage bottle is connected to the water discharge valve 23 by a thin hose. Both valves are opened for the discharge. Intermixing of the admitted air with the discharging sample water is thus prevented.

The bed water sampling device in accordance with the invention is a simple but reliable sampling device by which excellent measuring results can be obtained. This was demonstrated by internal tests by the applicant of a prototype of the claimed measuring device in the northern Atlantic Ocean at depths of 1,260 m and 2,500 m, as well as in the Bay of Eckernfoerde at a depth of 25 m, for such measuring parameters as methane, oxygen, the abundance of bacteria, nutrients, methane, radon 222 and sea water salt content at sampling times of a maximum of 7 minutes.

What is claimed is:

1. A bed water sampling device for simultaneously collecting a plurality of water samples from the lowest water column at different levels above a water bed with a plurality of cylindrical sample containers provided at least one end with a closure device actuated by a time-controlled release and arranged for vertical adjustment in a horizontal orientation on a center support rod terminating at one end in a ground element and connected at its opposite end to a steel cable for positioning on a water bed
   characterized by the fact that
   the center support rod (2) is connected at low friction and for free rotatability between a weighted base frame (7) as the ground element and the steel cable (9) at low friction and with a flow vane (6), that the time-controlled release (10) is mounted in the weighted base frame (7) in a compression proof manner and is activated automatically only by the placement continuing for a predetermined time on the water bed and that the sample containers (3) are provided at their other end (15) with a closure device (16) also actuated by the time-controlled release (10).

2. The bed water sampling device of claim 1,
   characterized by the fact that
   the two closure devices (16) of each sampling container (3) are provided with closure valves (17) which in the open state are connected against the bias of a rubber tension device (18) by a release shaft (21) latched by a corrosion wire (22), the corrosion wire being charged with electrical voltage leading to its rupture by activating the time controlled release (10).

3. The bed water sampling device of claim 1,
   characterized by the fact that
   each sampling container (3) is provided with a water discharge valve (23) and, positioned diametrically opposite, an air inlet valve (24).

4. The bed water sampling device of claim 1,
   characterized by the fact that
   the sampling container (3) is transparent.

5. The bed water sampling device of claim 1,
   characterized by the fact that
   the sampling containers (3) and both closure devices (16) are constructed to be compression proof.

6. The bed water sampling device of claim 1,
   characterized by the fact that
   a total of six sampling containers (3) are arranged at a height of 2 m and that each sampling container (3) has a filling capacity of 5 to 6 l.

7. The bed water sampling device of claim 1,
   characterized by the fact that
   above the sampling device (1) one or more buoyancy units are attached to a steel cable (9).

8. A bed water sampling device for simultaneously collecting
   a plurality of water samples from different levels of the lowest water column above a water bed, comprising:
   a plurality of tubular sampling containers forming openings at opposite ends thereof;
   means for simultaneously changing the openings from an open to a closed state in response to a predetermined signal;
   rotatable means for mounting the sampling containers in a horizontal orientation in a vertical arrangement;
   means connected to the mounting means for aligning the openings of the sampling containers in the direction of water current;
   means rotatably connected to the mounting means for placement on the water bed;

means connected to the mounting means opposite the rotatably connected means for raising and lowering the sampling device relative to the water bed; and means responsive to placing the sampling device on the water bed for generating the predetermined signal.

9. The sampling device of claim 8, wherein the means for simultaneously changing the openings from an open to a closed state comprises valve covers provided with means for biasing the valve covers to their closing position.

10. The sampling device of claim 9, wherein the biasing means comprises an elongate elastic member connected to the valve covers and extending through the tubular member.

11. The sampling device of claim 9, wherein the openings are maintained in their open state a latch releasable in response to the predetermined signal.

12. The sampling device of claim 11, wherein the latch is secured by a wire and the predetermined signal comprises an electric current for rupturing the wire.

13. The sampling device of claim 8, wherein the signal generating means comprises means responsive to the placing of the rotatably connected means on the water bed.

14. The sampling device of claim 13, wherein the signal generating means further comprises means for delaying generation of the predetermined signal for a predetermined interval of time after placement of the rotatably connected means on the water bed.

15. The sampling device of claim 8, wherein the rotatably connected member comprises a weighted frame member.

16. The sampling device of claim 15, wherein the weighted frame member is provided with an elongate shaft for rotatably receiving mounting means.

17. The sampling device of claim 16, wherein the means for lowering and raising the sampling device comprises a shackle with a cable connected thereto.

* * * * *